(12) United States Patent
Kaliaperumal et al.

(10) Patent No.: US 12,295,596 B2
(45) Date of Patent: May 13, 2025

(54) ASPIRATION CATHETER AND CLOT REMOVAL SYSTEM

(71) Applicant: Creganna Unlimited Company, Galway (IE)

(72) Inventors: Loganathan Kaliaperumal, Bangalore (IN); Ajay Chavan, Bangalore (IN)

(73) Assignee: Creganna Unlimited Company, Galway (IE)

( * ) Notice: Subject to any disclaimer, the term of this patent is extended or adjusted under 35 U.S.C. 154(b) by 404 days.

(21) Appl. No.: 17/749,590

(22) Filed: May 20, 2022

(65) Prior Publication Data

US 2023/0034091 A1   Feb. 2, 2023

(30) Foreign Application Priority Data

May 20, 2021   (IN) .............................. 202141022575

(51) Int. Cl.
*A61B 17/22* (2006.01)
*A61M 25/00* (2006.01)

(52) U.S. Cl.
CPC .... *A61B 17/22* (2013.01); *A61B 2017/22079* (2013.01); *A61M 25/0045* (2013.01); *A61M 25/005* (2013.01); *A61M 2025/0059* (2013.01)

(58) Field of Classification Search
CPC ......... A61B 17/22; A61B 2017/22079; A61M 25/0045; A61M 25/005; A61M 2025/0059
See application file for complete search history.

(56) References Cited

U.S. PATENT DOCUMENTS

| | | | |
|---|---|---|---|
| 5,403,292 A | 4/1995 | Ju | |
| 5,681,344 A | 10/1997 | Kelly | |
| 6,626,889 B1 | 9/2003 | Simpson et al. | |
| 10,531,883 B1* | 1/2020 | Deville | A61M 1/75 |
| 2016/0346506 A1* | 12/2016 | Jackson | A61M 25/0053 |

(Continued)

FOREIGN PATENT DOCUMENTS

| | | |
|---|---|---|
| WO | 2017074290 A1 | 5/2017 |
| WO | 2018033401 A1 | 2/2018 |
| WO | 2021068421 A1 | 4/2021 |

OTHER PUBLICATIONS

US FDA—510K Letter and Summary for Penumbra Inc, Jet7 intermediate aspiration catheter (dated Aug. 17, 2018). www.accessdata.fda.gov/cdrh_docs/pdf17/K173761.pdf (last accessed Aug. 21, 2024). (Year: 2018).*

(Continued)

*Primary Examiner* — Tan-Uyen T Ho
*Assistant Examiner* — Cherie M Poland
(74) *Attorney, Agent, or Firm* — Barley Snyder

(57) ABSTRACT

The present invention pertains to medical devices. More specifically, the present application is related to an aspiration catheter for a medical clot removal system and to a clot removal system comprising such an aspiration catheter. An aspiration catheter for a clot removal system has a distal section and a proximal section, wherein, in the distal section, a ratio of an outer diameter ($D_d$) and an open lumen inner diameter (ID) is in a range between 1.05 and 1.09, and wherein a volume of the aspiration catheter is in a range between 0.2 cubic inches and 0.4 cubic inches.

14 Claims, 4 Drawing Sheets

(56) References Cited

U.S. PATENT DOCUMENTS

2020/0022712 A1    1/2020  Deville et al.
2020/0129192 A1*  4/2020  Lin ........................ A61B 17/22

OTHER PUBLICATIONS

Li et al., "REACT Aspiration Catheters: Clinical Experience and Technical Considerations" Neurointervention. Jul. 2022; 17(2):70-77. ePub Jun. 20, 2022. PMID: 35718472 (Year: 2022).*

Extended European Search Report dated Sep. 30, 2022 corresponding to Application No. 22174007.9-1113, 19 pages.

Examination Report from the Intellectual Property Office (India) dated Dec. 19, 2022 corresponding to Application No. 202141022575, 5 pages.

* cited by examiner

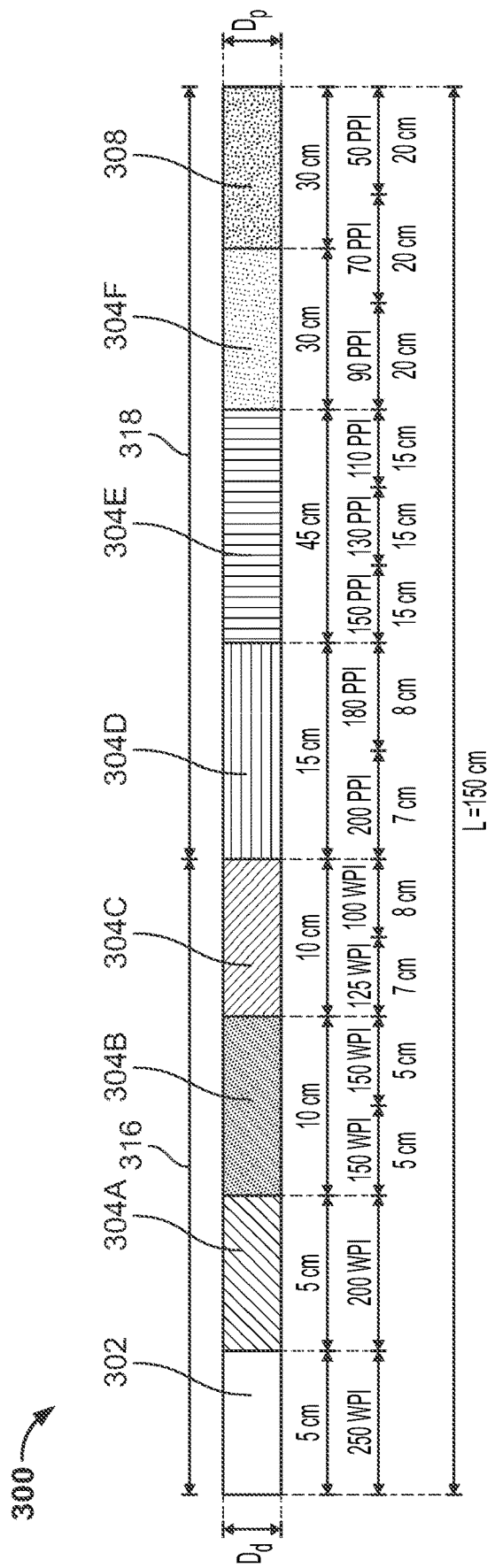
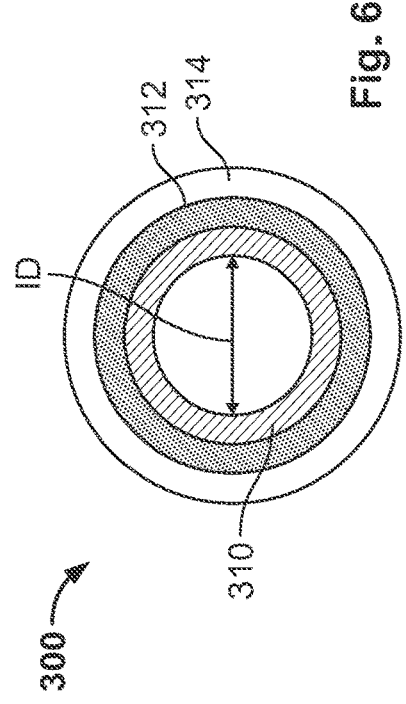
Fig. 5
Fig. 6

ASPIRATION CATHETER AND CLOT REMOVAL SYSTEM

CROSS-REFERENCE TO RELATED APPLICATIONS

This application claims the benefit of the filing date under 35 U.S.C. § 119(a)-(d) of Indian Patent Application No. 202141022575, filed May 20, 2021.

FIELD OF THE INVENTION

The present invention pertains to medical devices. More specifically, the present application is related to an aspiration catheter for a medical clot removal system and to a clot removal system comprising such an aspiration catheter.

BACKGROUND

Arterial and venous thromboembolic disease remains a major cause of death and disability. Strokes may be caused by a rupture or bleeding of a cerebral artery ("hemorrhagic stroke"), or a blockage in a cerebral artery due to a thromboembolism ("ischemic stroke"). Intracerebral hemorrhage (ICH) bleeding has long been associated with high rates of morbidity and mortality. Treatment choices for ICH are limited, and the effectiveness of currently available therapies is inadequate. Thrombolytics alone are not recommended, but are currently being investigated for use in conjunction with aspiration and other surgical techniques.

While intracranial hemorrhage is caused by blood clots located outside the blood vessels in the brain, Acute Ischemic Stroke (AIS) is caused by blood clots blocking a blood vessel in the brain arteries. Endovascular and outside of endovascular thromboembolic disease remain very widespread causes of death and disability with no ideally effective treatment currently available. Thus, there is a significant need for improved devices, methods and systems for treating thromboembolic disease.

There are many approaches for removing an embolus from the body, either surgical or using catheter devices for endovascular and outside endovascular removal of obstructive matter, such as blood clots, thrombus, atheroma, plaque and the like. These techniques are related to rotating baskets or impellers, cutters, high pressure fluid injections, Archimedes screw, vacuum, rotating wires and other means.

Removal of an embolus and blood clots from brain arteries are described using several devices and methods such as: embolectomy devices, clot pullers, retrieving devices or separating devices with aspiration. While most of these devices are capable of removing blood clots from the human arteries, there is still a clinical need for a simple, quick and easy access with devices to the treatment site through tortuous brain arteries, and safe removal of blood clots in a single pass. Often, catheters used to remove clots from brain arteries get clogged after partial removal of clots even under absolute vacuum. Thus, there is a need for more efficient and effective devices that facilitate a quick and single pass for the removal of thromboembolic material. It has been found that an aspiration catheter allowing a sufficient aspiration force may alleviate the problems with existing removal systems.

Therefore, there is a need to provide an aspiration catheter and clot removal system which improves therapeutic results and which can be fabricated economically, and at the same time be robust even in challenging application environments.

SUMMARY

The present disclosure provides an aspiration catheter for a clot removal system, the catheter having a distal section and a proximal section, wherein, in the distal section, a ratio of an outer diameter and an open lumen inner diameter is in a range between 1.05 and 1.09 inches, the lumen inner diameter is in a range between 0.077 inches and 0.081 inches, and wherein a volume of the catheter is in a range between 0.2 cubic inches and 0.4 cubic inches. The length of the catheter is in a range between 51 inches and 71 inches, It could be shown that with such an aspiration catheter an enhanced thrombus removal force and an enlarged thrombus entry area may be achieved. At the same time, the outer diameter is small enough to allow navigation into narrow passages.

BRIEF DESCRIPTION OF THE DRAWINGS

The accompanying drawings are incorporated into the specification and form a part of the specification to illustrate several embodiments of the present invention. These drawings, together with the description serve to explain the principles of the invention. The drawings are merely for the purpose of illustrating the preferred and alternative examples of how the invention can be made and used, and are not to be construed as limiting the invention to only the illustrated and described embodiments. Furthermore, several aspects of the embodiments may form—individually or in different combinations—solutions according to the present invention. The following described embodiments thus can be considered either alone or in an arbitrary combination thereof. The described embodiments are merely possible configurations and it must be borne in mind that the individual features as described above can be provided independently of one another or can be omitted altogether while implementing this invention. Further features and advantages will become apparent from the following more particular description of the various embodiments of the invention, as illustrated in the accompanying drawings, in which like references refer to like elements, and wherein:

FIG. 5 is a side view of an aspiration catheter according to a third example;

FIG. 6 is a sectional view of the aspiration catheter according to the third example;

DETAILED DESCRIPTION OF THE EMBODIMENT(S)

As used herein, the terms "proximal" and "distal" are to be taken as relative to a user using the disclosed aspiration devices. "Proximal" is to be understood as relatively closer to the user and "distal" is to be understood as relatively farther away from the user. Further, as this is generally known, the outer diameters of a catheter are given in F ("French"), 1 F being 0.0131233596 inches (0.3333333333 mm).

Figure 1:
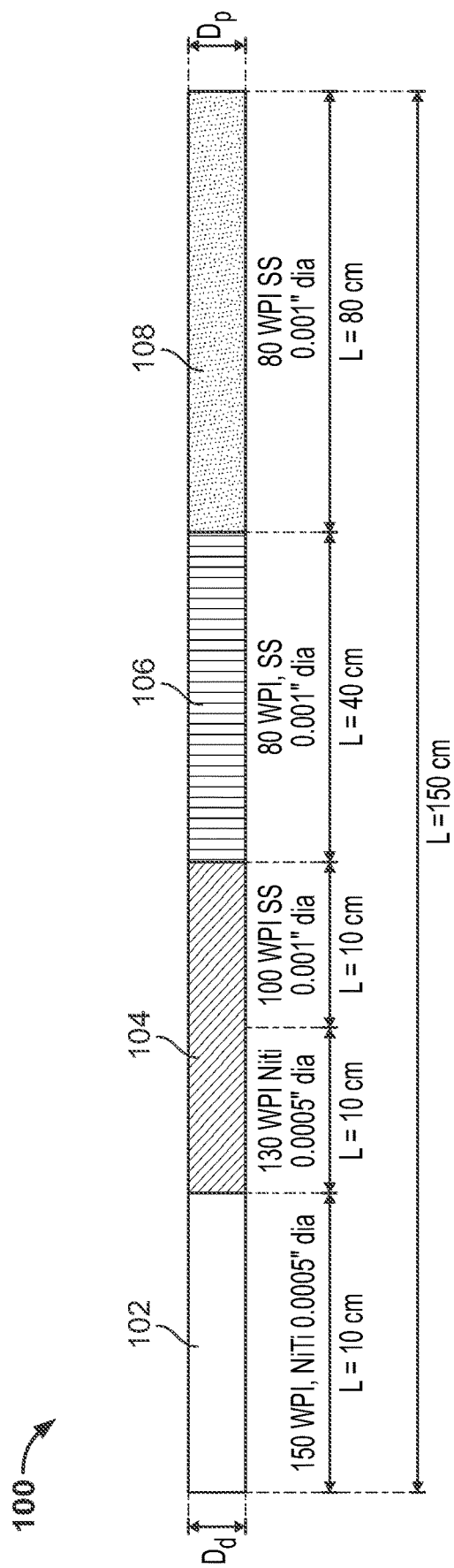
FIG. 1 is a side view of an aspiration catheter according to a first example.
Figure 2:
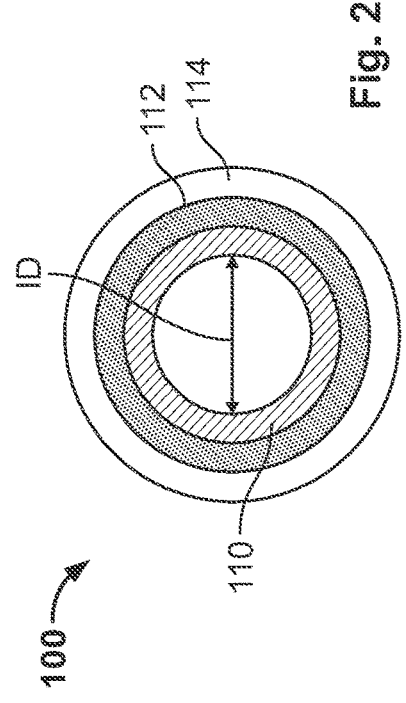
FIG. 2 is a sectional view of the aspiration catheter according to the first example.

In the following, the present invention will be described in detail with reference to the Figures, first referring to FIG. 1 and FIG. 2. FIG. 1 shows a schematic side view of an aspiration catheter 100 according to a first example, FIG. 2 shows a schematic cross sectional view of a distal section 102 of the catheter 100. It is important to note that in all the Figures the shown dimensions are highly schematic and may by no means be interpreted as being true to scale. In particular, the longitudinal dimensions of the catheter are represented in a shortened manner, whereas the layers of the cross section are exaggerated in their thickness.

As may be seen from FIG. 1, the aspiration catheter 100 comprises four different sections: Firstly the distal section 102, adjacent thereto a first intermediate section 104 and a second intermediate section 106. The proximal section 108 is arranged at the end of the aspiration catheter 100 which is connected to a drive device.

As can be seen from FIG. 2, the distal section 102 of the catheter 100 comprises three layers. The innermost layer is a liner 110 which may pass through the length of the catheter 100. For reinforcing the catheter 100, a reinforcement layer 112 is provided. An outer jacket 114 is arranged as the outermost layer encompassing the other layers. The inner diameter ID may for instance be as large as 0.079 inches.

According to the present disclosure, a distal outer diameter $D_d$ of 6.5 F can be achieved. This is possible by providing a comparatively low total thickness of the various layers, for instance by forming the reinforcement layer 112 as a Nitinol wire coil, the wire having a diameter of 0.0005 inches and a WPI count of 150. The outer jacket 114 in the distal section 102 is for instance formed by a PEBAX® layer with a shore hardness of 35D and a thickness of 0.0025 inches. The inner liner 110 is advantageously formed by a combination of an inner PTFE layer (e.g. 0.0005 inches) and a thinner outer layer of an aliphatic polyether-based thermoplastic elastomer such as Tecoflex® (0.0003 inches). In the shown example, the distal section has a length of 4 inches. The total length of the aspiration catheter 100 is chosen to be 59 inches, so that a total inner volume of 0.2895 cubic inches is obtained.

According to the present disclosure, each of the sections 102, 104, 106, 108 has a different outer jacket and/or reinforcement layer, but the identical liner is running along the complete length of the aspiration catheter 100.

For instance, the first intermediate section 104 is formed using a 55D shore hardness PEBAX® outer jacket having a thickness of 0.0025 inches. According to an advantageous example, the first intermediate section 104 is subdivided into two sub-sections wherein the first sub-section is reinforced by another Nitinol wire coil (diameter of 0.0005 inches and a WPI count of 130) and the second sub-section is reinforced by a stainless steel wire coil, the wire having a diameter of 0.001 inches and a WPI count of 100. The first intermediate section 104 may have a length of approximately 8 inches, each of the subsections having a length of approximately 4 inches.

Furthermore, adjacent to the first intermediate section 104, a second intermediate section 106 is arranged which has an outer jacket formed from a 63D PBAX® with a thickness of 0.0035 inches. The reinforcement layer of the second intermediate section 106 is for instance formed by a stainless steel wire coil having a diameter of 0.001 inches and a WPI count of 80. the second intermediate section 106 may have a length of 16 inches.

Finally, adjacent to the second intermediate section 106, the proximal section 108 is arranged, which may be brought into contact with the drive device. The proximal section 108 is the longest section (31.5 inches) and comprises a 72D PBAX® outer jacket with a thickness of 0.0035 inches. the reinforcement layer in the proximal section 108 is advantageously of the same type as in the second intermediate section 106, namely a stainless steel wire coil having a diameter of 0.001 inches and a WPI count of 80. The proximal section 108 does not have to have such an extremely small outer diameter $D_p$. In the present example, the outer diameter of the proximal section 108 has for instance 6.7 F.

With the above explained particular combination of materials, a sufficiently stable and steerable structure can be provided, at the same time achieving a particularly large inner diameter ID in combination with a small outer diameter $D_d$.

Figure 3:
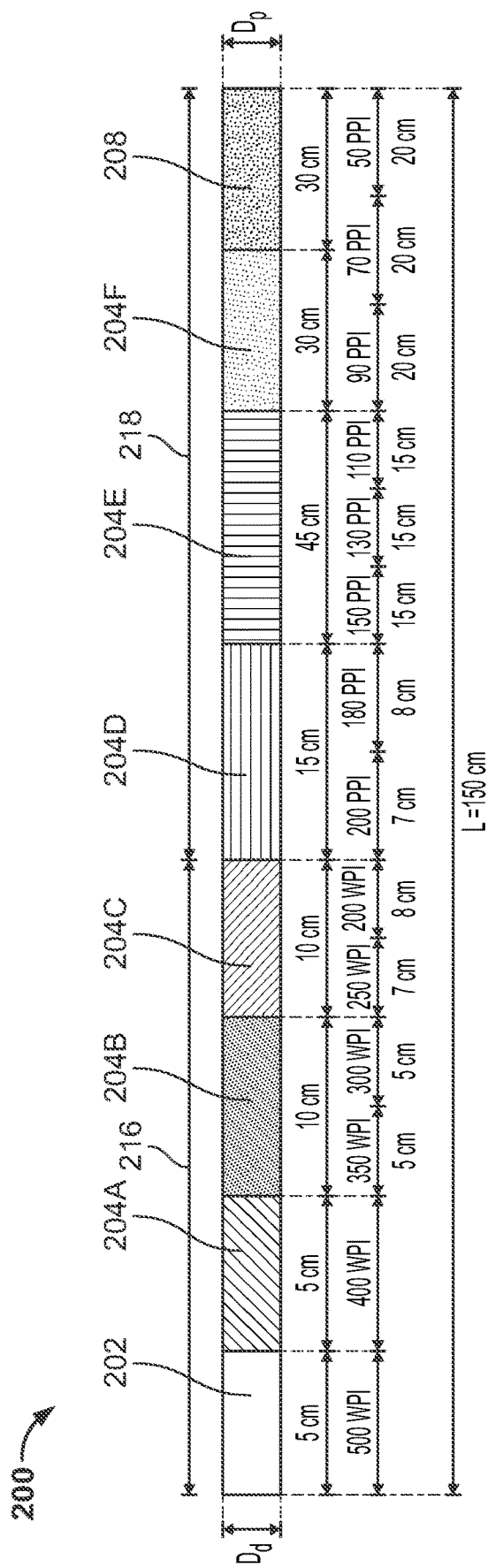
FIG. 3 is a side view of an aspiration catheter according to a second example.
Figure 4:
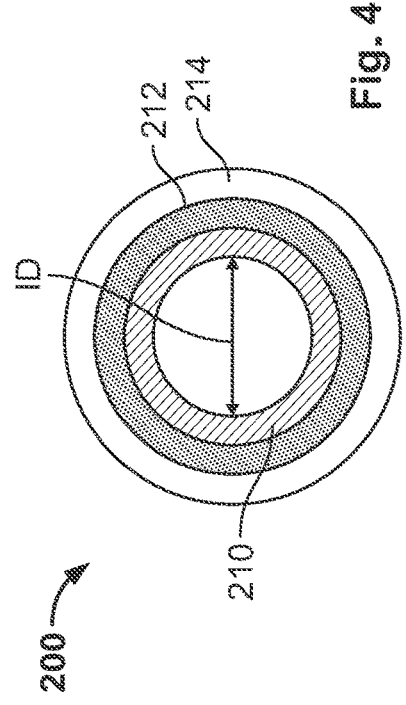
FIG. 4 is a sectional view of the aspiration catheter according to the second example.

Turning now to FIGS. 3 and 4, a further example of an aspiration catheter 200 will be explained in the following. The aspiration catheter 200 differs from the catheter 100 according to the first example in that a much greater variety of intermediate sections 204A to 204F is provided. Furthermore, not only wire coils are used for the reinforcement layers, but also wire braids. In particular, a coil zone 216 is provided within about 12 inches from the distal tip and a braid zone 218 is provided for the rest of the aspiration catheter 200. The coils in the coil zone 216 are formed from a Nitinol wire having a diameter of 0.0005 inches and varying wrap counts (WPI) as shown in FIG. 3.

In the braid zone 218, a stainless steel braiding is provided as the reinforcement layer with a DL load pattern of 0.0005 inches times 0.002 inches. The varying PPI counts are given in FIG. 3.

In the present example, the outer diameter $D_d$ of the distal section 202 is 6.5 F and the outer diameter $D_p$ of the proximal section 108 has for instance a value of 6.7 F. The total length of the aspiration catheter 200 is 59 inches. The inner diameter ID is 0.079 inches, so that a total inner volume of 0.2895 cubic inches is obtained.

The following table 1 summarizes the material characteristics for the aspiration catheter 200 of the second example.

TABLE 1

| Section | Outer jacket material | Shore hardness | Thickness |
| --- | --- | --- | --- |
| 202 | PEBAX ® | 25D | 0.002 inches |
| 204A | PEBAX ® | 35D | 0.002 inches |
| 204B | PEBAX ® | 45D | 0.0025 inches |
| 204C | PEBAX ® | 55D | 0.003 inches |
| 204D | PEBAX ® | 63D | 0.003 inches |
| 204E | PEBAX ® | 72D | 0.004 inches |
| 204F | Vestamid ® ME 71 | | 0.004 inches |
| 208 | Vestamid ML 21 | | 0.0045 inches |

In combination with the above materials for the outer jacket 214, a liner 210 is provided which comprises an inner layer of 0.0007 inches PTFE and an outer layer of 0.0002 inches Tecoflex®. Of course, any other liner material and material combination may also be used.

Advantageously, the aspiration catheter 200 has a further improved performance regarding distal flexibility, trackability, aspiration volume, and proximal stiffness.

Turning now to FIGS. 5 and 6, a further example of an aspiration catheter 300 will be explained in the following. The aspiration catheter 300 differs from the catheter 100 according to the first example in that a much greater variety of intermediate sections 304A to 304F is provided. Furthermore, not only wire coils are used for the reinforcement layers, but also a braiding. In particular, a coil zone 316 is provided within about 12 inches from the distal tip and a braid zone 318 is provided for the rest of the aspiration catheter 300. The coils in the coil zone 316 are formed from a Nitinol wire having a diameter of 0.0005 inches or a tungsten wire having a diameter of 0.0005 inches, the wire being applied with varying wrap counts (WPI) as shown in FIG. 5.

In the braid zone 318, a stainless steel braiding is provided as the reinforcement layer with a flat wire having a rectangular cross section of 0.0005 inches times 0.002 inches. The varying pics per inch (PPI) counts are given in FIG. 5. The third example differs from the second example by the particular values of the WPI and PPI counts.

In the example of FIGS. 5 and 6, the outer diameter $D_d$ of the distal section 302 is 6.5 F and the outer diameter $D_p$ of the proximal section 308 has for instance a value of 6.7 F. The total length of the aspiration catheter 300 is approximately 59 inches. The inner diameter ID is 0.079 inches, so that a total inner volume of 0.2895 cubic inches is obtained.

The following table 2 summarizes the material characteristics for the aspiration catheter 300 of the third example.

TABLE 2

| Section | Outer jacket material | Shore hardness | Thickness |
|---------|----------------------|----------------|-----------|
| 302     | PEBAX ®              | 25D            | 0.002 inches |
| 304A    | PEBAX ®              | 35D            | 0.002 inches |
| 304B    | PEBAX ®              | 45D            | 0.0025 inches |
| 304C    | PEBAX ®              | 55D            | 0.003 inches |
| 304D    | PEBAX ®              | 63D            | 0.003 inches |
| 304E    | PEBAX ®              | 72D            | 0.004 inches |
| 304F    | Vestamid ® ME 71     |                | 0.004 inches |
| 308     | Vestamid ML 21       |                | 0.0045 inches |

In combination with the above materials for the outer jacket 314, a liner 310 is provided which comprises an inner layer of 0.0007 inches PTFE and an outer layer of 0.0002 inches Tecoflex®. Of course, any other liner material and material combination may also be used.

Advantageously, the aspiration catheter 300 has a further improved performance regarding distal flexibility, trackability, and proximal stiffness. A highest thrombus removal force of 31.9 gf can be generated at a −29.2 inch Hg vacuum.

Figure 7:
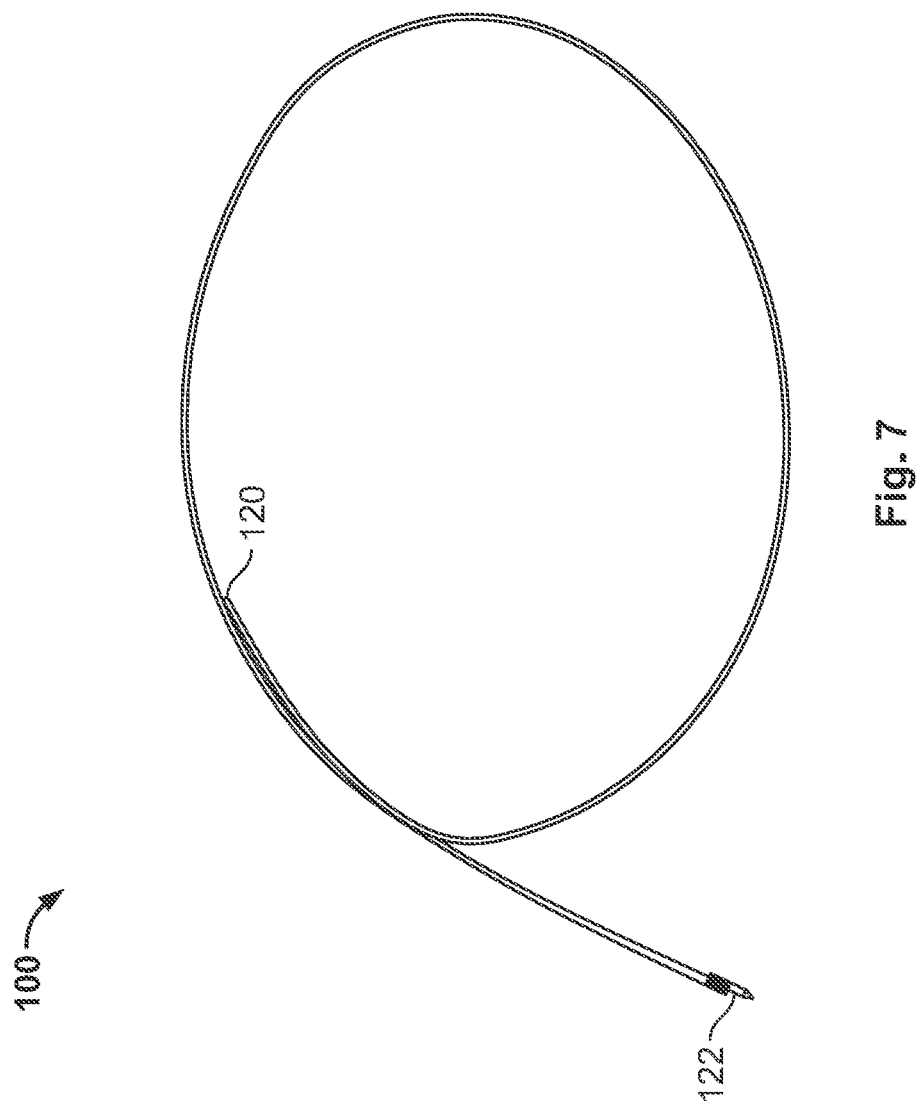
FIG. 7 is a perspective view of an aspiration catheter according to the first example of the present disclosure.

FIG. 7 illustrate a perspective view of an aspiration catheter 100 according to the first example, having a distal tip 120 and a proximal tip 122. The proximal tip 122 is formed to be connected to a drive unit comprising a vacuum pump. It should be noted that the aspiration catheters 200, 300 according to the second and third example will essentially look the same as the aspiration catheter 100 according to the first example.

As can be seen from FIG. 7, the longitudinal dimension of the catheter having for instance a length of approximately 59 inches is comparatively large, while the outer diameter at the distal tip 120 is very small.

As described above according to an advantageous example, in the distal section, the open lumen inner diameter is 0.079 inches and the outer diameter is 6.5 F, and wherein the total volume of the catheter is 0.2895 cubic inches, the catheter having a length of approximately 60 inches.

Additional advantageous characteristics of the aspiration catheter may be obtained by providing, in addition to the proximal and distal sections, one or more intermediate sections with different cross sectional geometries and characteristics compared to the proximal and distal sections. For example, the aspiration catheter may further comprise at least one intermediate section, wherein the distal section, the at least one intermediate section, and the proximal section are arranged adjacently, and wherein each section has an increasing wall thickness with the proximal section having the highest wall thickness. However, the thickness may also vary differently, i.e. being smaller at certain sections. Moreover, the one or more intermediate section may also differ from the distal and proximal section by physical and/or chemical characteristics, such as hardness, material composition and/or structure. For instance, the one or more intermediate sections may comprise different reinforcement layers, which differ in material and/or structure from the reinforcement layer of the adjacent sections. As reinforcement layers, coils or braids or slotted tubes made from various metals, e.g. Nitinol, a metal alloy of nickel and titanium which has a shape memory, tungsten, or stainless steel, or a combination of these materials may be used.

According to a further advantageous example, the distal section comprises an inner liner, a reinforcement layer encompassing the inner liner, and an outer jacket encompassing the reinforcement layer, wherein a total thickness of inner liner, the reinforcement layer, and the outer jacket is in a range between 0.0030 inches and 0.0050 inches. Such comparatively small wall thicknesses allow for a large open lumen inner diameter in combination with a low outer diameter, so that the aspiration catheter can be introduced into small vessels. For stabilizing such thin walls, the reinforcement layer may for instance be formed from a Nitinol coil having a comparatively high wraps per inch (WPI) count. For instance, a WPI count between 100 and 500 may be chosen.

In order to provide the open lumen throughout the catheter with a smooth and inert inner surface the inner liner may comprise a PTFE layer extending along all sections of the catheter.

As mentioned above, the reinforcement layer may comprise Nitinol, tungsten, or stainless steel, or a combination of these materials. Nitinol has the advantage of showing a shape memory effect, which is advantageous for controlling the maneuvering of the distal section of the catheter. In particular, the reinforcement layer in the distal section may comprise a coil, the coil being formed from a wire with a diameter of 0.0005 inches and a tightness of 150 to 500 wraps per inch.

According to the present disclosure, any suitable material may be chosen for the outer jacket in any of the sections. However, the inventors found that particularly advantageous characteristics may be achieved if the outer jacket comprises a layer of a polyamide material, e.g. polyether block amide (for instance PEBAX® or VESTAMID®) and/or if the outer jacket comprises a layer of an aliphatic polyether-based thermoplastic elastomer.

Furthermore, according to an advantageous example of the present disclosure, each of the distal section, the at least on intermediate section, and the proximal section have outer jackets with different thickness and/or hardness. For instance, a Shore hardness may vary between 35D and 72D. As this is known in the art, there are different Shore hardness scales for measuring the hardness of different materials and there is overlap on the different scales. For example, a material with a Shore hardness of 95 A is also a Shore 45D. The Shore D hardness scale measures the hardness of hard rubbers, semi-rigid plastics and hard plastics.

According to a further advantageous example, the reinforcement layer in at least one of the at least one intermediate section and the proximal section comprises a braid with a pic count in a range between 50 PPI and 300 PPI.

Furthermore, the reinforcement layer in at least one of the at least one intermediate section and the proximal section may comprise a coil with a coiling in a range between 100 WPI and 500 WPI.

In order to reach the desired inner volume of the aspiration catheter according to the present disclosure, the aspiration catheter is comparatively long, it may for instance have a total length of 1.50 m.

The present disclosure further provides a clot removal system (also referred to as a thromboembolic system) comprising an extraction device with an aspiration catheter according to the present disclosure and drive unit with a vacuum pump device. The clot removal system can be provided as a single unit with affixed components, or the components of the system may be detachable and attachable before, during or after the thromboembolic material removal procedure.

The devices and systems of the present disclosure relate to removal of thromboembolic material that include but are not limited to: clots, thrombus, atheroma, fluid, polyps, cysts or other obstructive matter from endovascular system. The endovascular system includes arteries, veins, previously implanted stents, grafts, shunts, fistulas and the like. Removal of thromboembolic materials may also include locations outside of the endovascular system such as: body organs, head, ureters, bile ducts, fallopian tubes, localized tumors, cancerous tissue removal or other particular target site. In the following, the term "clot removal system" is intended to cover all these applications.

In summary, the present disclosure provides a particularly advantageous ratio of the outer diameter $D_d$ in the distal section and the open lumen inner diameter ID, i.e. particularly close to the value 1. For instance, an inner diameter ID as large as 0.079 inches could be achieved for a 6.5 F outer diameter. The inner layer, the reinforcement layer and the outer layers are accommodated within a thickness of 0.0032 inches. According to the present disclosure, three different types of reinforcement may be used, namely Nitinol round wire with a diameter of 0.0005 inches, stainless steel 304V round wire with a diameter of 0.001 inches, and tungsten flat wire with a rectangular cross section of 0.0005 inches× 0.0015 inches.

The PPI range of the braid varies from 300 PPI to 50 PPI and the coiling WPI range varies from 100 WPI to 500 WPI. The particular variations along the longitudinal axis of the aspiration catheter gives designed performance output like distal flexibility, trackability, proximal stiffness and aspiration volume.

The outer jacket segment materials used in the particular sections and their specific lengths further contribute to the particular desired performance.

Advantageously, a maximum thrombus removal force of 31.9 gf can be generated by a 6.5 F outer diameter aspiration catheter at −29.2 inch Hg vacuum.

What is claimed is:

1. An aspiration catheter for a clot removal system, comprising a distal section and a proximal section,
   wherein, in the distal section, a ratio of an outer diameter (Da) and an open lumen inner diameter (ID) is in a range between 1.05 and 1.09,
   wherein a volume of the aspiration catheter is in a range between 0.2 cubic inches and 0.4 cubic inches; and
   further comprising at least one intermediate section, wherein the distal section, the at least one intermediate section, and the proximal section are arranged adjacently, each of the distal section, the at least one intermediate section, and the proximal section have outer jackets with different hardness, the distal section has the lowest hardness.

2. The aspiration catheter according to claim 1, wherein, in the distal section, the open lumen inner diameter (ID) is 0.079 inches and the outer diameter is 6.5 F, and wherein the total volume of the catheter is 0.2895 cubic inches for a total length of the catheter being 59 inches.

3. The aspiration catheter according to claim 1, wherein each section has an increasing wall thickness with the proximal section having the highest wall thickness.

4. The aspiration catheter according to claim 3, wherein the distal section comprises an inner liner, a reinforcement layer encompassing the inner liner, and the outer jacket encompassing the reinforcement layer wherein a total thickness of inner liner, the reinforcement layer, and the outer jacket is in a range between 0.0030 inches and 0.0050 inches.

5. The aspiration catheter according to claim 4, wherein the inner liner comprises a PTFE layer extending along all sections of the aspiration catheter.

6. The aspiration catheter according to claim 5, wherein the reinforcement layer comprises Nitinol and/or stainless steel and/or tungsten.

7. The aspiration catheter according to claim 6, wherein the outer jacket comprises a layer of a polyether block amide.

8. The aspiration catheter according to claim 7, wherein the outer jacket further comprises a layer of an aliphatic polyether-based thermoplastic elastomer.

9. The aspiration catheter according to claim 8, wherein the reinforcement layer in the distal section comprises a coil, the coil being formed from a wire with a diameter of 0.0005 inches and a tightness of 150 wraps per inch to 500 wraps per inch, wherein the wire is manufactured from Nitinol or stainless steel or tungsten or a combination thereof.

10. The aspiration catheter according to claim 4, wherein the reinforcement layer in at least one of the at least one intermediate section and the proximal section comprises a braid with a pick per inch count in a range between 50 PPI and 300 PPI.

11. The aspiration catheter according to claim 4, wherein the reinforcement layer in at least one of the at least one intermediate section and the proximal section comprises a coil with a coiling in a range between 100 WPI and 500 WPI.

12. The aspiration catheter according to claim 9, wherein the aspiration catheter has a total length of 59 inches.

13. The aspiration catheter according to claim 1, wherein the distal section comprises the outer jacket comprising a layer of polyamide material.

14. A clot removal system comprising the aspiration catheter according to claim 1 and a vacuum pump device.

* * * * *

UNITED STATES PATENT AND TRADEMARK OFFICE
CERTIFICATE OF CORRECTION

| | |
|---|---|
| PATENT NO. | : 12,295,596 B2 |
| APPLICATION NO. | : 17/749590 |
| DATED | : May 13, 2025 |
| INVENTOR(S) | : Loganathan Kaliaperumal et al. |

It is certified that error appears in the above-identified patent and that said Letters Patent is hereby corrected as shown below:

In the Claims

Claim 1, Column 7, Line 59, "(Da) and an open lumen inner diameter (ID) is in a" should read -- (Dd) and an open lumen inner diameter (ID) is in a --

Signed and Sealed this
Fifteenth Day of July, 2025

Coke Morgan Stewart
*Acting Director of the United States Patent and Trademark Office*